US00PP35941P3

(12) United States Plant Patent
Neu et al.

(10) Patent No.: US PP35,941 P3
(45) Date of Patent: Jul. 2, 2024

(54) ***PELARGONIUM* PLANT NAMED 'KLEPZ22698'**

(50) Latin Name: ***Pelargonium peltatum* (L.) L'Hér. ex Aiton x *Pelargonium zonale* (L.) L'Hér. ex Aiton**
Varietal Denomination: KLEPZ22698

(71) Applicant: KLEMM + SOHN GMBH & CO. KG, Stuttgart (DE)

(72) Inventors: Nina Neu, Weissach im Tal (DE); Martin Glawe, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/312,468

(22) Filed: May 4, 2023

(65) Prior Publication Data

US 2023/0371414 P1 Nov. 16, 2023

(30) Foreign Application Priority Data

May 16, 2022 (CH) ..... 22-3525

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324, 325
CPC . A01H 5/02; A01H 5/00; A01H 6/425; A01H 6/42
See application file for complete search history.

(56) References Cited

PUBLICATIONS

Issuu Huiskula Taimitukku Taimiluettelo 2023 retrieved on Oct. 10, 2023 online at https://issuu.com/huiskulaoy/docs/huiskula_taimiluettelo_2023_web, 3 pp. (Year: 2022).*
Pentland Plants retrieved on Oct. 10, 2023 at https://www.pentlandplants.co.uk/downloads/pentland-plants-catalogue-2023.pdf, 3 introductory pages, pp. 1-5, 49, 71-72, 1 back page. (Year: 2023).*
Selecta One 2023/2024 retrieved on Oct. 10, 2023 at https://selecta-one.com/katalog/index.php?catalog=Spring_Trixi_2023_24_NE, one cover page and p. 66. (Year: 2023).*
Google English translation of Huiskula Taimitukku Taimiluettelo, one page. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new *Pelargonium* plant particularly distinguished by red flower color with a light pink border and center, a lack of zonation and a large flower size, is disclosed.

1 Drawing Sheet

Genus and species: *Pelargonium peltatum* (L.) L'Hér. ex Aiton x *Pelargonium zonale* (L.) L'Hér. ex Aiton.
Variety denomination: 'KLEPZ22698'.

CROSS-REFERENCE TO RELATED APPLICATION

This patent application claims the benefit of priority from Switzerland Plant Breeders Rights Application No. 22-3525 as filed on May 16, 2022, the contents of which is incorporated herein by reference for all it teaches and discloses.

BACKGROUND OF THE NEW PLANT

The present invention comprises a new and distinct variety of *Pelargonium*, botanically known as *Pelargonium peltatum* (L.) L'Hér. ex Aiton x *Pelargonium zonale* (L.) L'Hér. ex Aiton and hereinafter referred to by the variety name 'KLEPZ22698'. 'KLEPZ22698' originated from a controlled cross in August 2016 in Nairobi, Kenya between the proprietary female *Pelargonium* variety 'PIZ-2014-4307' (unpatented) and the proprietary male *Pelargonium* variety 'PIZ-2014-4308' (unpatented).

Seeds from the controlled cross were obtained. The seeds were sown and plants were grown for evaluation. A single plant was selected in June 2017 and subsequently named 'KLEPZ22698'. In July 2017 'KLEPZ22698' was first vegetatively propagated by vegetative stem cuttings in Stuttgart, Germany. 'KLEPZ22698' was found to reproduce true to type in successive generations of asexual propagation via stem cuttings in Stuttgart, Germany.

SUMMARY

The following are the most outstanding and distinguishing characteristics of this new variety when grown under normal horticultural practices in Latina, Italy.

1. Red flower color with a light pink border and center;
2. A lack of zonation; and
3. A large flower size.

DESCRIPTION OF THE PHOTOGRAPH

This new *Pelargonium* plant is illustrated by the accompanying photograph which shows an overall view of the plant in a pot. The photograph is of an approximately 14-week-old plant grown indoors in Stuttgart, Germany, in April 2021. The colors shown are as true as can be reasonably obtained by conventional photographic procedures.

DESCRIPTION OF THE NEW VARIETY

The following detailed descriptions set forth the distinctive characteristics of 'KLEPZ22698'. Data was collected on 19-week-old plants in Latina, Italy under greenhouse conditions in April 2023. Color references are to The R.H.S. Colour Chart of The Royal Horticultural Society of London (R.H.S.), 5edition (2007).

Classification:
- *Family.*—*Geraniaceae.*
- *Botanical.*—*Pelargonium peltatum* (L.) L'Hér. ex Aiton x *Pelargonium zonale* (L.) L'Hér. ex Aiton.
- *Common.*—*Pelargonium.*
- *Designation.*—'KLEPZ22698'.

Parentage:
- *Female parent.*—'PIZ-2014-4307' (unpatented).
- *Male parent.*—PIZ-2014-4308 (unpatented).

Plant:
- *Form.*—Bushy.
- *Habit.*—Upright.
- *Height* (*from top of soil*).—22.5 cm.
- *Width* (*horizontal plant diameter*).—26.0 cm.
- *Natural flowering season.*—March to October.
- *Propagation type.*—Vegetative by stem cuttings.
- *Time to produce a finished flowering plant.*—12 weeks.
- *Time to initiate and develop roots.*—4 weeks.
- *Root description.*—Fine, dense, white (RHS N155C).

Stems:
- *Quantity of stems per plant.*—5 to 6.
- *Color.*—RHS 146C with partially RHS 178A.
- *Surface texture.*—Pubescent.
- *Stem form.*—Round.
- *Diameter.*—1.0 cm.
- *Length.*—7.0 to 12.0 cm.
- *Internode length.*—1.2 cm.
- *Anthocyanin.*—Present (RHS 165A).

Leaves:
- *Arrangement.*—Alternate.
- *Shape.*—Reniform.
- *Apex.*—Round.
- *Base.*—Open.
- *Margin.*—Crenate.
- *Surface texture both surfaces.*—Pubescent.
- *Length.*—7.0 cm.
- *Width.*—8.3 cm.
- *Color.*—Upper surface: RHS 147A. Lower surface: RHS 146A.
- *Zonation.*—None.
- *Depth of sinus.*—1.9 cm.
- *Petiole.*—Length: 4.3 cm. Diameter: 0.3 cm. Color: RHS 146C. Strength: Medium.
- *Venation pattern.*—Palmate.
- *Venation color.*—Upper surface: RHS 147A. Lower surface: RHS 146C.

Inflorescence:
- *Lastingness of flowers on the plant.*—6 to 8 days.
- *Umbels.*—Quantity of umbels per plant 4 to 5. Length 7.0 cm. Diameter: 12.5 cm.
- *Individual florets of the umbel.*—Quantity of florets per umbel: 25 to 30. Depth: 1.0 cm. Diameter: 6.0 cm.
- *Fragrance.*—Absent.

Flower buds:
- *Cluster shape.*—Round.
- *Cluster size.*—Length: 2.0 cm. Width: 3.0 cm.
- *Surface texture.*—Pubescent.
- *Bud.*—Height: 1.1 cm. Width: 0.5 cm. Shape: Elliptic. Apex: Acute. Base: Obtuse. Margin: Entire. Color: RHS 146A.

Petals:
- *Quantity per flower.*—5.
- *Shape.*—Spatulate.
- *Apex.*—Round.
- *Base.*—Obtuse.
- *Margin.*—Entire.
- *Length.*—3.4 cm.
- *Width.*—3.0 cm.
- *Markings.*—Upper petal: Strong, single spot that tapers at the base of the petal. Lower petal: Strong, single spot that tapers at the base of the petal. Petal overlap: Moderate.
- *Surface texture.*—Upper surface: Smooth. Lower surface: Smooth.
- *Color of lobes.*—Upper lobes: Upper surface: RHS 45B marking, RHS 68A background color and apex margin area, RHS 62C at the base. Lower surface: RHS 62D. Lower lobes: Upper surface: RHS 45B marking, RHS 68A background color and apex margin area, RHS 62C at the base. Lower surface: RHS 62D.

Petaloids: Absent.

Sepals:
- *Number per flower.*—5.
- *Shape.*—Elliptic.
- *Apex.*—Acute.
- *Base.*—Obtuse.
- *Margin.*—Entire.
- *Surface texture.*—Upper surface: Smooth. Lower surface: Pubescent.
- *Color.*—Upper surface: RHS 146B with RHS 166A at the base. Lower surface: RHS 146B with RHS 165A at the base.
- *Length.*—1.3 cm.
- *Width.*—0.5 cm.
- *Reflex.*—Absent.

Pedicel:
- *Length.*—3.8 cm.
- *Diameter.*—0.2 cm.
- *Color.*—*RHS* 166A.
- *Surface texture.*—Pubescent.
- *Strength.*—Medium.
- *Swelling.*—Absent.

Peduncle:
- *Length.*—13.8 cm.
- *Diameter.*—0.5 cm.
- *Color.*—RHS 146B and partially RHS 166A.
- *Texture.*—Pubescent.
- *Strength.*—Strong.

Reproductive organs:
- *Stamens.*—Quantity per flower: 5. Anther length: 0.2 cm. Filament length: 0.7 cm. Filament color: RHS N155A with RHS N66B at the tips. Pollen amount: Abundant. Pollen color: RHS 169A.
- *Pistils.*—Number: 1. Stigma color: RHS 58B. Style length: 0.2 cm. Style color: RHS 58B. Ovary arrangement: Central. Ovary color: RHS 166A. Ovary diameter: 0.2 cm Ovary length: 0.6 cm. Ovary Texture: Pubescent.

Fruit and seed set: None observed.

Disease and pest/insect resistance: None observed.

COMPARISON WITH PARENTAL LINES AND KNOWN VARIETY

'KLEPZ22698' is distinguished from its parents as described in Table 1.

TABLE 1

Comparison with Parental Lines

| Characteristic | 'KLEPZ22698' | Female parent | Male parent |
|---|---|---|---|
| Flower color | Red with light pink border and center | White pink eye | White pink eye |

'KLEPZ22698' can be compared to the commercial variety Savannah® 'TexMex Fire' (patent status unknown). Differences between the two varieties are described in Table 2:

TABLE 2

Comparison with Similar Variety

| Characteristic | 'KLEPZ22698' | Savannah ® 'TexMex Fire' |
|---|---|---|
| Flower Color | Red with light pink border and center | Red with purple pink border and light pink center |
| Flower Size | Big | Medium |

We claim:

1. A new and distinct cultivar of *Pelargonium* Plant Named 'KLEPZ22698' as described and illustrated herein.

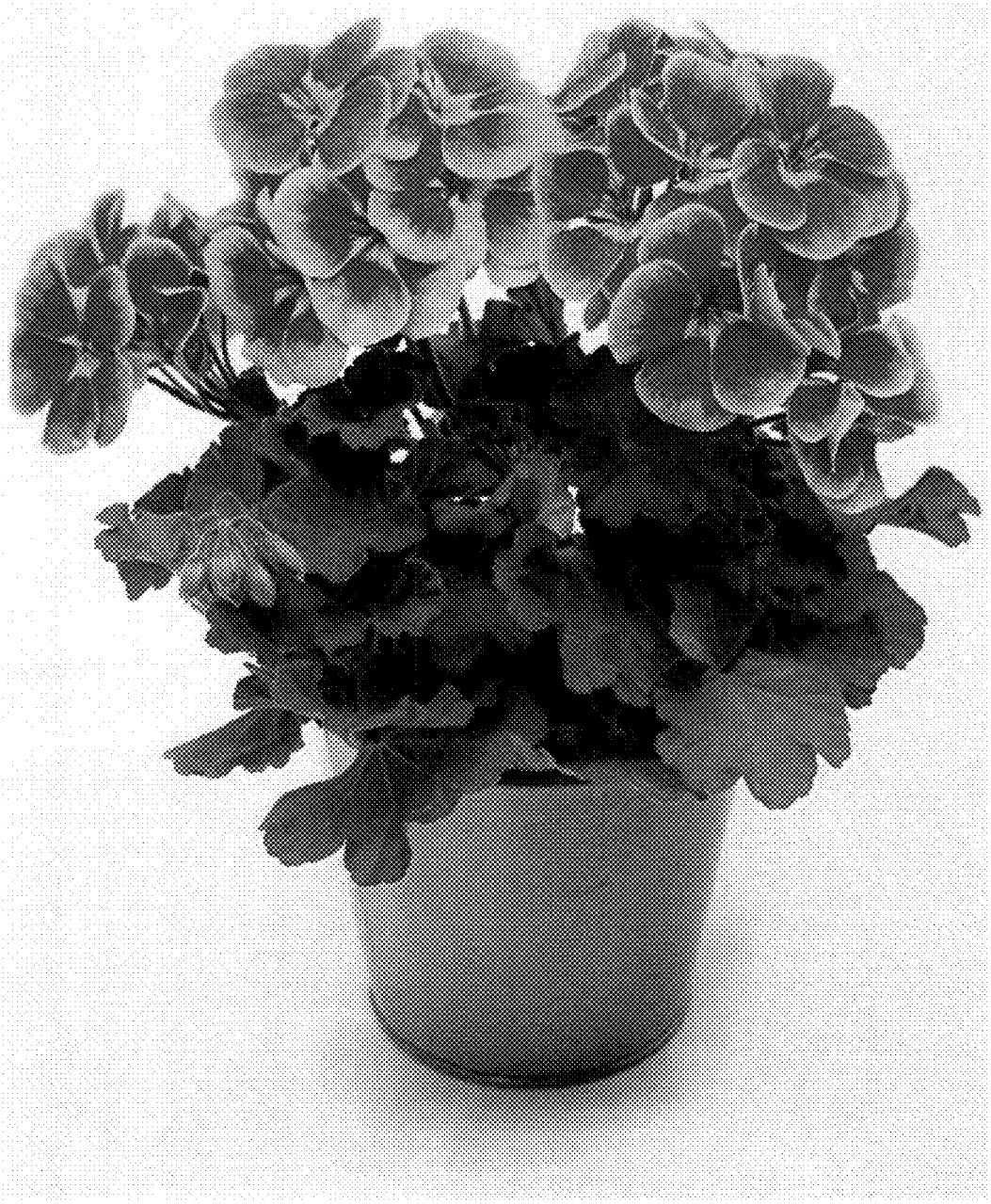

* * * * *